US006934359B2

(12) United States Patent
Chen et al.

(10) Patent No.: US 6,934,359 B2
(45) Date of Patent: *Aug. 23, 2005

(54) WAVELENGTH DISPERSIVE XRF SYSTEM USING FOCUSING OPTIC FOR EXCITATION AND A FOCUSING MONOCHROMATOR FOR COLLECTION

(75) Inventors: Zewu Chen, Ballston Lake, NY (US); David M. Gibson, Voorheesville, NY (US)

(73) Assignee: X-Ray Optical Systems, Inc., East Greenbush, NY (US)

( * ) Notice: Subject to any disclaimer, the term of this patent is extended or adjusted under 35 U.S.C. 154(b) by 8 days.

This patent is subject to a terminal disclaimer.

(21) Appl. No.: 10/742,414

(22) Filed: Dec. 19, 2003

(65) Prior Publication Data

US 2004/0131146 A1 Jul. 8, 2004

Related U.S. Application Data

(63) Continuation of application No. PCT/US02/19272, filed on Jun. 18, 2002.
(60) Provisional application No. 60/299,371, filed on Jun. 19, 2001.

(51) Int. Cl.[7] .............................................. G01N 23/223
(52) U.S. Cl. ........................................ 378/84; 378/45
(58) Field of Search ............................. 378/45–50, 84, 378/85

(56) References Cited

U.S. PATENT DOCUMENTS

| | | | | |
|---|---|---|---|---|
| 4,562,585 A | * | 12/1985 | Gobel et al. ................... | 378/83 |
| 4,599,741 A | | 7/1986 | Wittry .......................... | 378/85 |
| 5,175,755 A | | 12/1992 | Kumakhov | |
| 5,192,869 A | | 3/1993 | Kumakhov | |
| 5,406,609 A | | 4/1995 | Arai et al. ..................... | 378/73 |
| 5,497,008 A | | 3/1996 | Kumakhov ............... | 250/505.1 |
| 5,570,408 A | | 10/1996 | Gibson | |
| 5,604,353 A | | 2/1997 | Gibson et al. | |
| 5,745,547 A | | 4/1998 | Xiao | |
| 5,892,809 A | | 4/1999 | Wittry .......................... | 378/85 |
| 5,982,847 A | | 11/1999 | Nelson ......................... | 378/47 |
| 6,285,506 B1 | | 9/2001 | Chen | |
| 6,317,483 B1 | | 11/2001 | Chen | |
| 6,697,454 B1 | * | 2/2004 | Nicolich et al. .............. | 378/85 |

FOREIGN PATENT DOCUMENTS

| | | |
|---|---|---|
| EP | 0 339 713 A1 | 11/1989 |
| EP | 0 724 150 A1 | 7/1996 |
| WO | WO 01/39211 A1 | 5/2001 |
| WO | WO 02/25258 A1 | 3/2002 |

OTHER PUBLICATIONS

Chen, Z.W. et al., "Microprobe X–Ray Fluorescence With The Use of Point–Focusing Diffractors," Appl. Phys. Lett., vol. 71, No. 13, Sep. 29, 1997, pp. 1884–1886 (XP–000725822).

* cited by examiner

*Primary Examiner*—Craig E. Church
(74) *Attorney, Agent, or Firm*—Jeffrey R. Klembczyk, Esq.; Kevin P. Radigan, Esq.; Heslin Rothenberg Farley & Mesiti, P.C.

(57) ABSTRACT

X-ray fluorescence (XRF) spectroscopy systems and methods are provided. One system includes a source of x-ray radiation and an excitation optic disposed between the x-ray radiation source and the sample for collecting x-ray radiation from the source and focusing the x-ray radiation to a focal point on the sample to incite at least one analyte in the sample to fluoresce. The system further includes an x-ray fluorescence detector and a collection optic comprising a doubly curved diffracting optic disposed between the sample and the x-ray fluorescence detector for collecting x-ray fluorescence from the focal point on the sample and focusing the fluorescent x-rays towards the x-ray fluorescence detector.

57 Claims, 4 Drawing Sheets

WAVELENGTH DISPERSIVE XRF SYSTEM USING FOCUSING OPTIC FOR EXCITATION AND A FOCUSING MONOCHROMATOR FOR COLLECTION

CROSS-REFERENCE TO RELATED PATENTS/APPLICATIONS

This application is a continuation of PCT application PCT/US02/19272 filed Jun. 18, 2002, and published under PCT Article 21(2) in English as WO 02/103710 A2 on Dec. 27, 2002. PCT/US02/19272 claimed the priority of U.S. provisional application 60/299,371, filed Jun. 19, 2001. The entire disclosures of both are incorporated herein by reference. This application also contains subject matter which relates to the subject matter of the following commonly-owned patents and applications, each of which is hereby incorporated herein by reference in its entirety:

"Use Of A Kumakhov Lens For X-Ray Lithography", by Muradin A. Kumakhov, U.S. Pat. No. 5,175,755, issued Dec. 29, 1992;

"Device For Controlling Beams Of Particles, X-Ray and Gamma Quanta", by Muradin A. Kumakhov, U.S. Pat. No. 5,192,869, issued Mar. 9, 1993;

"Use Of A Kumakhov Lens In Analytic Instruments", by Muradin A. Kumakhov, U.S. Pat. No. 5,497,008, issued Mar. 5, 1996;

"High Intensity, Small Diameter X-Ray Beam, Capillary Optic System", by David M. Gibson, U.S. Pat. No. 5,570,408, issued Oct. 29, 1996;

"Multiple-Channel, Total-Reflection Optic With Controllable Divergence", by Gibson et al., U.S. Pat. No. 5,604,353, issued Feb. 18, 1997;

"Multiple Channel Optic", by Qi-Fan Xiao, U.S. Pat. No. 5,745,547, issued Apr. 28, 1998;

"Curved Optical Device and Method Of Fabrication", by Zewu Chen, U.S. Pat. No. 6,285,506, issued Sep. 4, 2001;

"Doubly Curved Optical Device With Graded Atomic Planes", by Zewu Chen, U.S. Pat. No. 6,317,483, issued Nov. 13, 2001;

"Total-Reflection X-Ray Fluorescence Apparatus and Method Using a Doubly-Curved Optic", by Zewu Chen, U.S. Ser. No. 09/667,966, filed Sep. 22, 2000; and "X-Ray Tube and Method and Apparatus for Analyzing Fluid Streams Using X-Rays", by Radley et al., U.S. Ser. No. 60/336,584, filed Dec. 4, 2001.

FIELD OF THE INVENTION

The field of the present invention relates to x-ray fluorescence (XRF) spectroscopy systems, and in particular, to a system and method which include focusing x-ray optical elements for forming a focusing excitation beam on samples and monochromators for collecting secondary x-rays from the sample.

BACKGROUND OF THE INVENTION

X-ray fluorescence (XRF) spectroscopy is widely recognized as a very accurate method of determining the atomic composition of a material, achieved by irradiating a sample with x-rays and observing the resulting secondary x-rays emitted by the sample.

In general, XRF systems consist of a source of excitation radiation (an x-ray tube or a radioisotope), a means to detect secondary x-rays from the sample and determine their energy or wavelength, and a display of the spectral output. The intensity of the secondary x-rays at certain energies or wavelengths is correlated to the elemental concentration in the sample. Computer software is often used to analyze the data and determine the concentration.

The process begins by irradiating the sample using a source of x-rays. As x-ray photons strike the sample, they knock electrons out of the inner shell of the atoms that make up the sample, creating vacancies that destabilize the atoms. The atoms stabilize when electrons from the outer shell are transferred to the inner shells, and in the process give off characteristic x-ray photons whose energy is the difference between the two binding energies of the corresponding shells. There are two conventional approaches to determining the x-ray spectrum emitted from the sample. The first approach is energy dispersive spectrometry (EDS), and the second is wavelength dispersive spectrometry (WDS). In an energy dispersive spectrometry system, an energy dispersive detector, such as a solid-state detector or a proportional counter, is used to determine the energy spectrum of the emitted photons from the sample. In a wavelength spectrometry system, a crystal or a multi-layer structure is used to select a specific x-ray wavelength from the x-rays photons emitted from the sample.

X-ray fluorescence using EDS is the most widely used method of elemental concentration analysis. This method has some advantages. First, the EDS detector can detect almost all of the elements in the periodic table at once. Second, the system is compact because an additional optic is not required on the collection side compared to wavelength dispersive x-ray fluorescent systems. Third, a low-power x-ray tube may be used because the EDS detector has a large collection solid angle and high efficiency. There are disadvantages to XRF/EDS systems, however, including relatively poor sensitivity and poor energy resolution. Also, because the EDS detector sees all of the x-rays from the sample, the detector is easily saturated by the fluorescent signal from the major elements and the strong scattering of the primary beam.

X-ray fluorescence using WDS has several advantages also, including higher energy resolution and higher signal-to-background ratio compared with XRF/EDS systems. Thus, the XRF/WDS approach is a powerful tool for trace element analysis and applications that require high energy resolution. However, there are disadvantages to conventional XRF/WDS systems, including a requirement for a high power x-ray tube due to limitations of the WDS approach that result in a low efficiency, and a small collection solid angle. Another disadvantage of a conventional WDS system is that the crystal or multi-layer structure on the collection side only selects a specific x-ray wavelength and a scanning mechanism or multi-crystal system is needed for multi-element detection. This has the advantage that detector saturation may be avoided, but it results in a complicated alignment. Therefore, XRF/WDS systems are typically bulky, complex, and more expensive as compared to XRF/EDS systems.

U.S. Pat. No. 5,982,847 to Nelson discloses an energy dispersive (EDS) system, using only polychromatic optics in both the detection and collection paths. No mention is made of diffracting optics in either the excitation or collection paths.

WO02/25258 to X-Ray Optical Systems, Inc. is also strictly an EDS system. Even though monochromatic excitation is used—the detection path is not limited to specific wavelengths with a detection optic—there is no detection optic disclosed or taught by this document. Therefore, the detection system encounters a broader band of wavelengths and processes this broader band using conventional EDS techniques.

EP 0339713 to N. V. Philips discloses a WDS system, however as discussed above, this document discloses the conventional technique of illuminating a very large sample area, a pinhole/slit 6 to define the angle of incidence upon optic 22, thus severely limiting the collection solid angle. There is no disclosure, teaching or suggestion of a focusing optic, providing a small sample spot size, and the attendant advantages of the present invention. The small sample spot size of the present invention is "placed" at position 6, but without limiting the collection solid angle of the detection optic.

Chen, et al, "Microprobe X-Ray Fluorescence with the Use of Point-Focusing Diffractors," Appl. Phys Lett. 71 (13) 1884–1886, September 1997 is similar to WO02/25258, discussed above. Even though monochromatic excitation is used—the detection path is not limited to specific wavelengths with a detection optic—there is no detection optic disclosed or taught by this document.

U.S. Pat. No. 5,406,609 to Arai et al. is also similar to WO02/25258 —monochromatic excitation with a standard EDS detection scheme.

While most XRF instruments are generally for the analysis of a wide range of elements, there are many important applications in industry process control that require single element or limited element detection. Thus, the present invention is directed to providing compact XRF/WDS systems that provide an ultra high sensitivity or high speed analysis for a limited number of elements.

SUMMARY OF THE INVENTION

The shortcomings of the prior approaches are overcome, and additional advantages are provided, by the present invention which in one aspect comprises an x-ray fluorescence (XRF) spectroscopy system. The XRF system includes at least one source of x-ray radiation and at least one excitation optic disposed between the at least one x-ray radiation source and the sample. The at least one excitation optic collects x-ray radiation from the at least one source and focuses the x-ray radiation to a focal point on the sample to incite at least one analyte in the sample to fluoresce. The system further includes at least one x-ray detector and at least one collection optic. The at least one collection optic comprises at least one doubly curved diffracting optic disposed between the sample and the at least one x-ray detector for collecting x-ray fluorescence from the focal point on the sample and directing the fluorescent x-rays towards the at least one x-ray detector.

Numerous enhancements on the above-described XRF spectroscopy system are also described and claimed herein. For example, the at least one source of x-ray radiation could comprise at least one electron bombardment x-ray source. The at least one excitation optic could comprise at least one focusing polychromatic optic, for example, one or more polycapillary optics, and/or could comprise at least one focusing monochromatic optic. The focusing monochromatic optic(s) could comprise at least one doubly curved crystal and/or at least one doubly curved multi-layer optic. The focal point could have a focal spot size of less than 500 microns, and the sample could be a solid or a fluid. Further the sample could be a petroleum based product, such as gasoline, diesel, crude oil or lubrication oil. The at least one analyte to be incited within the sample could comprise sulfur and/or iron. In addition, the x-ray radiation focused on the sample may be incident on the sample at an angle less than the angle of total external reflection, as desirable for total reflection x-ray fluorescence (TXRF), or the x-ray radiation focused on the sample may be incident on the sample at an angle greater than the angle of total external reflection, as desirable for normal x-ray fluorescence.

Further enhancements may include the at least one collection optic directing x-rays of the at least one analyte towards the detector(s) for determining concentration of the at least one analyte in the sample or a thickness of the sample. Further, the at least one doubly curved diffracting optic of the at least one collection optic could comprise at least one doubly curved crystal. The at least one doubly curved crystal could have a Johann geometry, a Johannson geometry, a partial Johannson geometry approximation, or could comprise a logarithmic spiral crystal optic. Still further, the at least one doubly curved diffracting optic could comprise at least one doubly curved multi-layer optic, which could be a doubly curved graded optic, or a doubly curved logarithmic spiral optic in certain embodiments. Still further, the at least one collection optic could be fixed relative to the sample and the at least one x-ray detector. The at least one x-ray detector could be one or more gas proportional counters, one or more scintillation counters, and/or one or more solid state detectors. The one or more solid state detectors could comprise at least one PIN diode solid state detector.

In another aspect, an x-ray fluorescence spectroscopy (XRF) method is disclosed. This method includes: providing at least one source of x-ray radiation; providing at least one excitation optic disposed between the at least one x-ray radiation source and a sample to be analyzed for collecting x-ray radiation from the at least one source and focusing the x-ray radiation to a focal point on the sample to incite at least one analyte in the sample to fluoresce; providing at least one x-ray detector; and disposing at least one collection optic, comprising at least one doubly curved diffracting optic, between the sample and the at least one x-ray detector for collecting x-ray fluorescence from the focal point on the sample and focusing the fluorescent x-rays towards the at least one x-ray detector.

Additional features and advantages are realized through the techniques of the present invention. Other embodiments and aspects of the invention are described in detail herein and are considered a part of the claimed invention.

BRIEF DESCRIPTION OF THE DRAWINGS

The subject matter which is regarded as the invention is particularly pointed out and distinctly claimed in the claims at the conclusion of the specification. The foregoing and other objects, features, and advantages of the invention are apparent from the following detailed description taken in conjunction with the accompanying drawings in which:

BEST MODE FOR CARRYING OUT THE INVENTION

Figure 1:
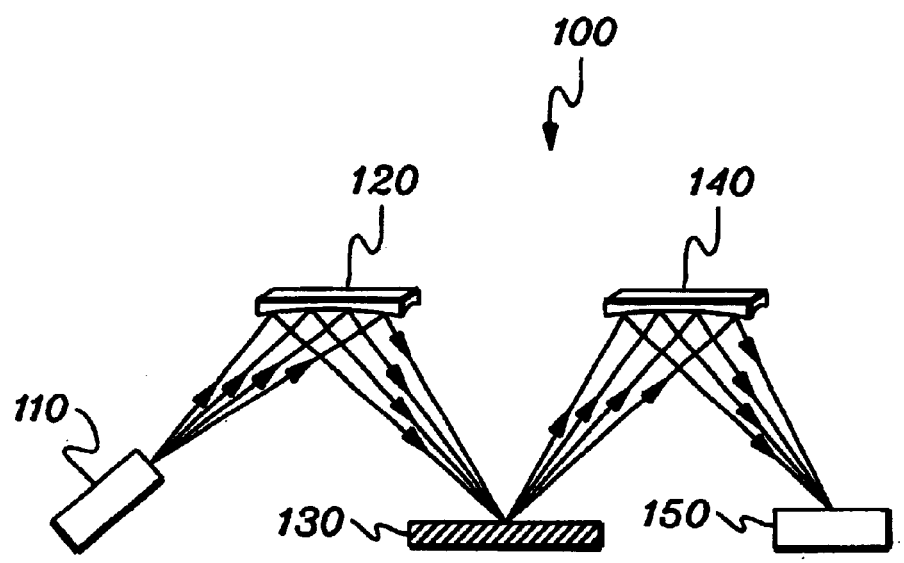
FIG. 1 shows one embodiment of an XRF/WDS system 100, in accordance with an aspect of the present invention.

Generally stated, one embodiment of a compact XRF/WDS system in accordance with an aspect of the present invention comprises an x-ray source, an excitation x-ray optic that focuses x-rays onto a sample from the source, at least one collection monochromator and an x-ray counter. The excitation x-ray optic can be a focusing polycapillary optic that provides polychromatic excitation or a point-focusing doubly curved crystal optic that provides monochromatic excitation. The collection monochromator (which can be a doubly curved crystal optic, a doubly curved multi-layer optic, or other doubly curved diffracting optic) selects a desired characteristic wavelength of an element. The intensity of the reflected x-rays is measured by a detector and is correlated to the concentration of this element in the specimen.

One aspect of an XRF/WDS system in accordance with the present invention is that the excitation optic can efficiently capture a large cone angle of x-rays from a point x-ray source. This optic is a focusing optic which can produce a very intensive excitation beam on the sample even with the use of a compact, low-power (e.g., <1 KW, and more beneficially <100 W) x-ray source. The use of a low-power x-ray tube makes this system much more compact and simpler compared with a conventional XRF/WDS system using a bulky kw x-ray tube.

Another aspect of this invention is that a monochromatic excitation beam can be produced if a doubly curved crystal optic is used as the excitation optic. In a typical embodiment of an XRF/WDS system, a polychromatic beam is used to excite the sample. Monochromatic excitation gives much higher signal-to-background ratio than polychromatic excitation due to the elimination of the scattering bremsstrahlung from the x-ray source on the sample. This improves the detection limit of the system significantly. Monochromatic excitation also greatly simplifies the quantitative analysis of XRF.

Still another aspect of this invention is that the excitation beam is focused on the sample because of the focusing capability of the excitation optic. The focal spot size of the beam on the sample may be in the range of $50\mu$ to $500\mu$, which is about two orders of magnitude smaller that the beam size of a conventional system (which is typically ~10 mm–30 mm). Besides providing efficient collection, this smaller beam size allows spatial resolution in the analysis.

Due to the smaller sample excitation area, a doubly curved diffracting optic can be efficiently used as the collection optic (in another aspect of the present invention). Doubly curved monochromatic optics can provide large collection solid angles from a spot. (In a conventional XRF/WDS system with a large excitation beam size, a flat or singly curved monochromator is the choice and the collection solid angle is limited.) A doubly curved monochromator improves the signal level considerably for the detected element for a given geometry and intensity of the excitation beam.

A further aspect of this invention is that the collection optic can be fixed relative to the sample and the detector, with no moving parts involved. This could have both advantage and disadvantage. An advantage would be that it speeds up the analysis and improves system reliability, while a disadvantage is that multiple collection optics may be necessary; for example, for multi-element analysis.

To restate, in accordance with the principles of the present invention, an XRF/WDS system is described with x-ray focusing optics providing polychromatic or monochromatic excitation to a sample. Secondary x-rays that result from x-ray fluorescence are collected by a monochromator, which comprises a doubly curved diffractor, for forwarding to a detector such as a proportional counter, a room temperature PIN detector, or a NaI detector. One example of an XRF/WDS system 100 using such x-ray optics to provide monochromatic excitation and collect x-rays from the sample is described in detail below with reference to FIG. 1.

XRF/WDS system 100 includes, for example, a low power x-ray source 110, a monochromatic focusing optic 120, a sample 130, a collection monochromator 140, and a detector 150.

Low power x-ray source 110 (e.g., <1 KW, and more ideally <100 W) is a source of x-ray radiation such as an x-ray tube, a sealed source of radioactive material, or a source of high energy electrons that impinge upon a metal target and produce x-ray radiation. One example of low power x-ray source 110 is a 50 W x-ray tube, with a target material comprising chrome, copper, tungsten, or molybdenum, and an electron beam size on the target material in the range of approximately 50 $\mu$m to 300 $\mu$m.

Sample 130 is a material to undergo metrology measurements. An example of sample 130 may be a process flow such as diesel fuel from which measurement of the concentration of sulfur is desired, or lubricating oil from which measurement of the concentration of wear metal (iron) is desired. If sample 130 is a fluid flow, a window material (not shown) may be included to enable transmission of x-ray excitation radiation into and x-ray fluorescence out of sample 130.

Monochromatic focusing optic 120, located between x-ray source 110 and sample 130 of XRF system 100, serves to reflect or transmit only radiation within a small range of energies to sample 130, e.g. within a range of energies between tens or hundreds of electron-Volts, as opposed to polychromatic optics, which transmit radiation with energy bandwidths in the thousands of electron-Volts. Optic 120 also focuses the x-rays to a small focal spot on sample 130. The size of this focal spot may be in the range of 50 $\mu$m to 500 $\mu$m.

One example of focusing optic 120 is a Johann type doubly curved crystal. An example of the geometry of a Johann type doubly curved crystal is shown in FIG. 2. In this geometry, the diffracting planes of the crystal 160 are shown parallel to the crystal surface. The crystal surface, which is a toroidal shape, has the Johann geometry in the plane of the focal circle 170 and axial symmetry along line SI, where point S is the location of the x-ray source 110 (FIG. 1) and point I is the focal spot. The crystal surface has a radius of curvature of 2R in the plane of the focal circle and a radius of curvature of $2R \sin^2 \theta_B$ in the mid-plane perpendicular to segment SI, where R is the radius of the focal circle and $\theta_B$ is the Bragg angle. X-rays diverging from point S, and striking the crystal surface with incident angles within the rocking curve width of the crystal will be reflected efficiently to point I. This type of doubly curved crystal not only provides point focusing but also monochromatizing of beam 180 since only x-rays photons with the correct wavelength can be reflected.

Figure 2:
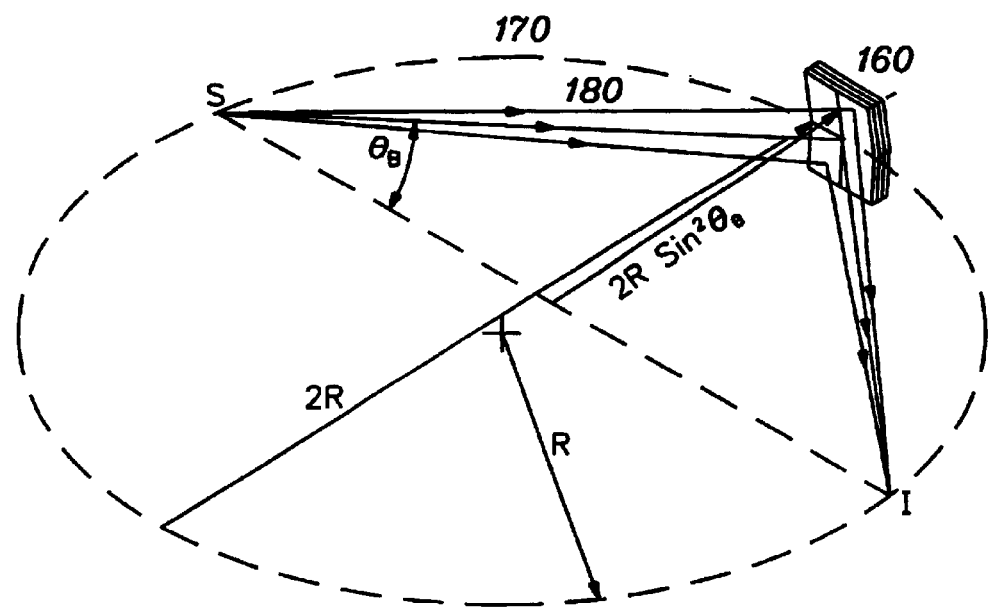
FIG. 2 shows a doubly curved crystal optic which provides point-to-point focusing for use in a system in accordance with the present invention.

As shown in FIG. 1, x-ray optic 140 is another monochromating optical element of XRF system 100, and is located between sample 130 and detector 150. This optic collects a specific wavelength of x-rays and directs the x-rays to an x-ray detector. In a conventional XRF/WDS system, a flat or singly-curved crystal optic might be the optic of choice. In the present invention, the collection monochromator is a doubly curved diffractor (e.g., a crystal or multi-layer optic), which can provide a much larger collection solid angle from a point than can a flat/singly-curved optic.

Figure 3A:
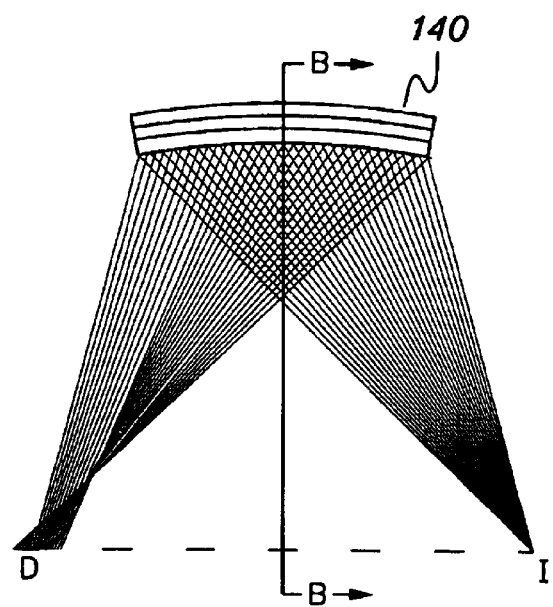
FIG. 3A shows one embodiment of the geometry of a doubly curved logarithmic spiral crystal or multi-layer optic for use in a system in accordance with the present invention.
Figure 3B:
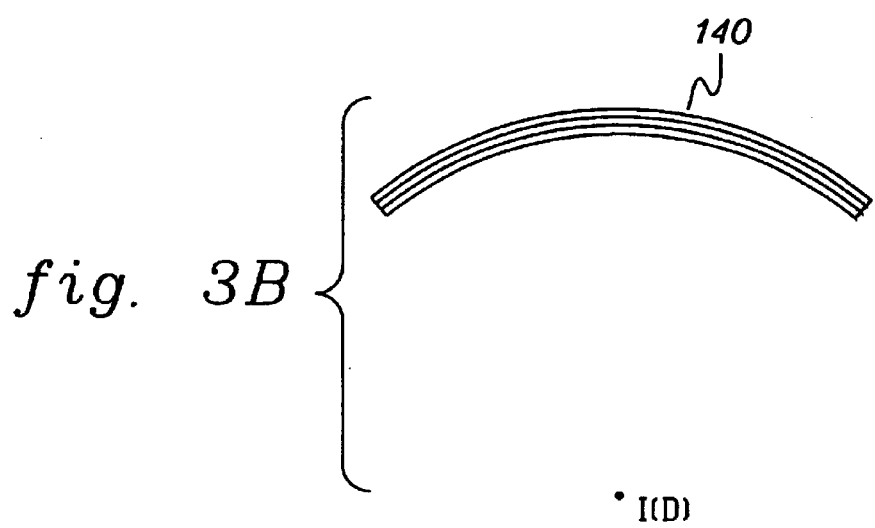
FIG. 3B depicts a cross-sectional view of the optic of FIG. 3A taken along line B—B.

A specific example of a collection monochromatic optic 140 is a doubly curved logarithmic spiral crystal optic. One embodiment of this geometry is illustrated in FIGS. 3A & 3B. In this geometry, the diffraction planes of the crystal optic are parallel to the crystal surface. The crystal surface in the dispersive plane has the shape of a logarithmic spiral and a rotational symmetry about the axis ID, where point I is the origin of the log spiral and the focal point of the excitation beam on the sample 130 (FIG. 1), and point D is the location of the detector 150 (FIG. 1). Fluorescence x-rays emitted from point I on the sample surface have a constant incident angle on this logarithmic spiral surface due to the property of the spiral curve. This constant angle is selected to be the Bragg angle of the characteristic x-rays of the interested element in the sample 130 for the diffraction planes of the crystal. The reflected x-rays from the doubly curved log spiral geometry will not form to a point, but to a caustic in the dispersive plane. The x-rays will be focused on the axis ID, as shown in FIG. 3B, along the direction of ID.

Alternately, multilayer optics may be employed in the system of FIG. 1 for monochromatic optic 120 and monochromatic optic 140. Detector 150 may be a simple counting detector, namely, a gas proportional counter, a scintillation counter, or a room temperature PIN diode solid state detector.

Advantageously, XRF/WDS system 100 is well suited for high-sensitivity trace elemental analysis. The point-to-point focusing doubly curved crystal optic provides a large collection solid angle and forms a very intense focusing monochromatic beam on the sample even with the use of a low power x-ray tube. Due to the monochromatic excitation, the signal-to-background ratio is improved significantly and the detection sensitivity is improved. Point focusing of the excitation beam onto the sample enables the efficient use of a doubly curved collection optic to improve the collection solid angle of the fluorescence x-rays. This will further improve sensitivity of the system.

As one specific embodiment of XRF/WDS system 100 of FIG. 1, the system could comprise an x-ray source 110 comprising a 50 W x-ray tube with a source material of chrome, copper, tungsten or molybdenum, and a spot size on the source material that is approximately 100 μm to 300 μm. The optic 120 may be a doubly curved point focusing crystal that is fabricated from silicon, germanium, or other crystal materials and is located 100 mm to 200 mm from the x-ray source 110 along the optical axis, which is defined as the ray proceeding central from the x-ray source impinging upon doubly curved crystal 120 central to the doubly curved crystal 120. The sample 130 may be oil, for example, with trace elements that may include sulfur, vanadium, and nickel. Sample 130 may be located 100mm to 200 mm from the monochromatic optic 120 measured along the optical axis. Second monochromatic optic 140 may be a doubly curved log spiral crystal that is fabricated from silicon, germanium, or other crystal materials, and is located 100 mm to 200 mm from sample 130 measured along the optical axis. A detector 150 may be a gas proportional counter, a scintillation counter, a room temperature PIN detector, or a NaI detector and be located 100 mm to 200 mm from the sample measured along the optical axis.

By adding one or more collection monochromators and detectors to system 100, two or more elements can be detected, with each collection monochromator paired to a detector for a respective, single element detection.

Figure 4:
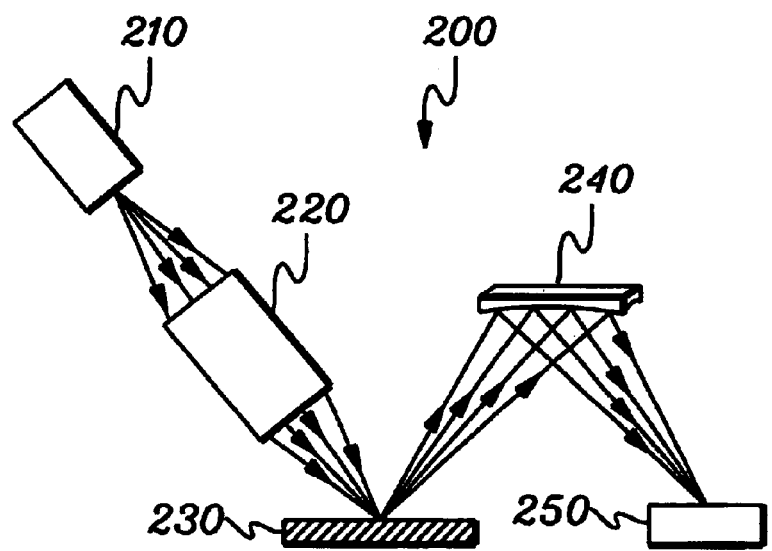
FIG. 4 depicts another embodiment of an XRF/WDS system 200, in accordance with an aspect of the present invention.

FIG. 4 shows an alternative embodiment of an XRF system 200 in accordance with an aspect of the present invention. System 200 includes a source 210, a polychromatic focusing optic 220, a sample 230, a doubly curved monochromatic optic 240, and a detector 250.

Figure 5:
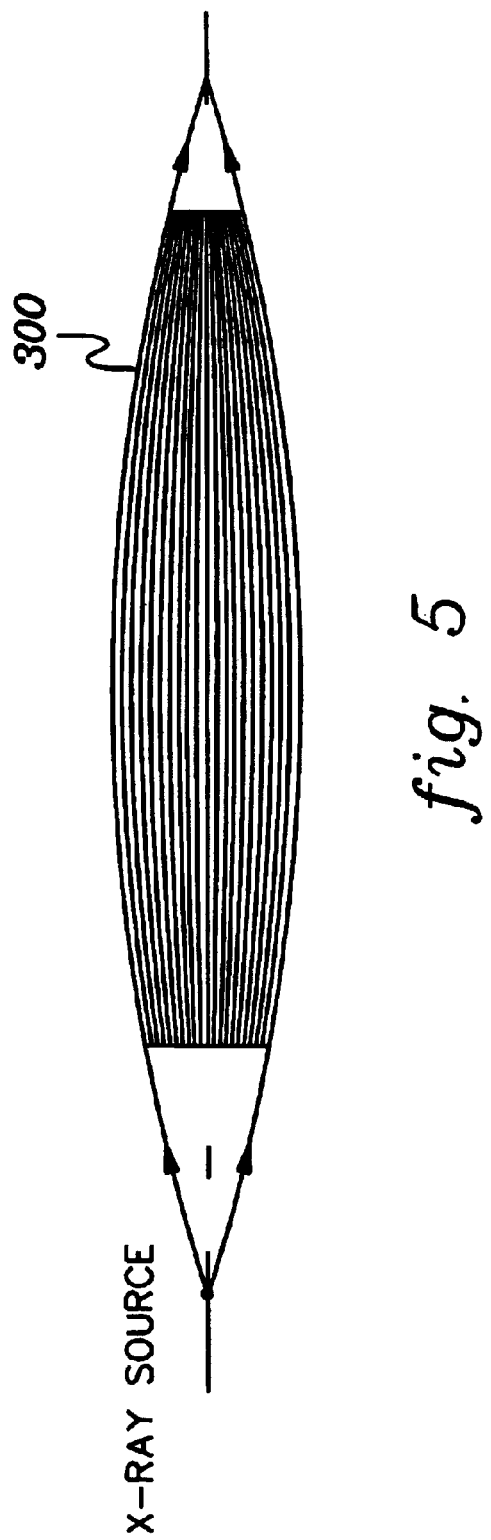
FIG. 5 shows a polycapillary optic which provides point-to-point focusing, for use in a system in accordance with an aspect of the present invention.

Polychromatic optic 220 is an optical element which transmits a broad range of photon energies, while focusing the photons it collects to a small spot on sample 230. One example of a polychromatic optic that is well suited to function as optic 220 is a polycapillary optic 300 (see FIG. 5), such as available from X-Ray Optical Systems, of Albany, N.Y. A polycapillary optic, which is described in detail in many of the above-incorporated patents, is a bundle of thin, hollow tubes that transmit photons via total reflection.

Due to the polychromatic excitation, the signal-to-background ratio will be poorer than compared to that of system 100 (FIG. 1). However, system 200 (FIG. 4) can provide several advantages. For example, with system 200 a smaller focal spot can be obtained due to the better focusing capability of a polycapillary optic. This may give better spatial resolution for local analysis. For example, a 20 μm to 50 μm focal spot can be obtained using a 50 W x-ray tube and polycapillary optic. Another advantage is that polychromatic excitation provides x-ray photons with a wide range of energy that can cover almost all the elements in the periodic table.

In one specific embodiment, XRF/WDS system 200 may include an x-ray source 210 which may be a 50 W x-ray tube with a source material of chrome, copper, tungsten or molybdenum and a spot size on the target material that is approximately 100 μm to 300 μm. The polychromatic optic 220 may be a polycapillary optic located 30 mm to 50 mm from x-ray source 210. The sample 230 may be, for example, oil with elements that may include sulfur, vanadium, and nickel. The sample 230 could be located 100 mm to 200 mm from polycapillary optic 220. Doubly curved monochromator 240 may be a doubly curved log spiral crystal that is fabricated from silicon, germanium, or other crystal material and is located 100 mm to 200 mm from the sample 230 measured along the optical axis. Detector 250 could be is a gas proportional counter, a scintillation counter, a room temperature PIN detector, or a NaI detector located 100 mm to 200 mm from the monochromatic optic 240 measured along the optical axis. Multiple collection monochromators with corresponding detectors could also be used for multi-element detection.

Although preferred embodiments have been depicted and described herein, it will be apparent to those skilled in the relevant art that various modifications, additions, substitutions and the like can be made without departing from the spirit of the invention as defined in the following claims.

What is claimed is:

1. An x-ray fluorescence (XRF) spectroscopy system comprising:
   at least one source of x-ray radiation;
   at least one x-ray detector;
   at least one monochromating collection optic comprising
      at least one doubly curved diffracting optic disposed between a sample and the at least one x-ray detector for collecting x-ray fluorescence from a focal point on the sample and directing the fluorescent x-rays of a characteristic energy of a predetermined analyte towards the at least one x-ray detector; and at least one excitation optic disposed between the at least one x-ray radiation source and the sample for collecting x-ray radiation from the at least one source and focusing the x-ray radiation to the focal point on the sample to incite said analyte in the sample to fluoresce.

2. The XRF spectroscopy system of claim 1, wherein the at least one source of x-ray radiation comprises at least one electron bombardment x-ray source.

3. The XRF spectroscopy system of claim 1, wherein the at least one excitation optic comprises at least one focusing polychromatic optic.

4. The XRF spectroscopy system of claim 3, wherein the at least one focusing polychromatic optic comprises at least one polycapillary optic.

5. The XRF spectroscopy system of claim 1, wherein the at least one excitation optic comprises at least one focusing monochromatic optic.

6. The XRF spectroscopy system of claim 5, wherein the at least one focusing monochromatic optic comprises at least one doubly curved crystal.

7. The XRF spectroscopy system of claim 5, wherein the at least one focusing monochromatic optic comprises at least one doubly curved multi-layer optic.

8. The XRF spectroscopy system of claim 1, wherein the focal point has a focal spot size less than 500 microns.

9. The XRF spectroscopy of claim 1, wherein the x-ray radiation focused on the sample is incident on the sample at an angle less than the angle of total external reflection.

10. The XRF spectroscopy of claim 1, wherein the x-ray radiation focused on the sample is incident on the sample at an angle greater than the angle of total external reflection.

11. The XRF spectroscopy system of claim 1, wherein the sample comprises a solid.

12. The XRF spectroscopy system of claim 1, wherein the sample comprises a fluid.

13. The XRF spectroscopy system of claim 12, wherein the fluid comprises a petroleum based product.

14. The XRF spectroscopy system of claim 13, wherein the petroleum based product comprises gasoline or diesel.

15. The XRF spectroscopy system of claim 13, wherein the petroleum based product comprises crude oil.

16. The XRF spectroscopy system of claim 11, wherein petroleum based product comprises lubrication oil.

17. The XRF spectroscopy system of claim 1, wherein the at least one analyte comprises sulfer.

18. The XRF spectroscopy system of claim 1, wherein the at least one analyte comprises iron.

19. The XRF spectroscopy system of claim 1, wherein the at least one collection optic directs x-rays of the analyte towards the at least one x-ray detector for determining concentration of the analyte in the sample or a thickness of the sample.

20. The XRF spectroscopy system of claim 1, wherein the at least one doubly curved diffracting optic comprises at least one doubly curved crystal.

21. The XRF spectroscopy system of claim 20, wherein the at least one doubly curved crystal comprises at least one doubly curved crystal having Johann geometry.

22. The XRF spectroscopy system of claim 20, wherein the at least one doubly curved crystal comprises at least one doubly curved crystal having Johannson geometry or partial Johannson geometry approximation.

23. The XRF spectroscopy system of claim 20, wherein the at least one doubly curved crystal comprises at least one doubly curved logarithmic spiral crystal optic.

24. The XRF spectroscopy system of claim 1, wherein the at least one doubly curved diffracting optic comprises at least one doubly curved multi-layer optic.

25. The XRF spectroscopy system of claim 24, wherein the at least one doubly curved multi-layer optic comprises at least one doubly curved logarithmic spiral optic.

26. The XRF spectroscopy system of claim 1, wherein the at least one doubly curved diffracting optic comprises at least one doubly curved graded diffracting optic.

27. The XRF spectroscopy system of claim 1, wherein the at least one collection optic is fixed relative to the sample and is fixed relative to the at least one x-ray detector.

28. The XRF spectroscopy system of claim 1, wherein the at least one x-ray detector comprises at least one gas-proportional counter.

29. The XRF spectroscopy system of claim 1, wherein the at least one x-ray detector comprises at least one scintillation counter.

30. The XRF spectroscopy system of claim 1, wherein the at least one x-ray detector comprises at least one solid state detector.

31. The XRF spectroscopy system of claim 30, wherein the at least one solid state detector comprises at least one PIN diode solid state detector.

32. The XRF spectroscopy system of claim 1, wherein the at least one x-ray detector comprises a non-energy-sensitive detector.

33. The XRF spectroscopy system of claim 1, wherein the at least one doubly curved diffracting optic is positioned such that an input focal point thereof at the focal point of the sample corresponds to an output focal point of the at least one excitation optic.

34. An (XRF) spectroscopy method comprising:

providing at least one source of x-ray radiation;

providing at least one x-ray detector;

disposing at least one monochromating collection optic, comprising at least one doubly curved diffracting optic, between the sample and the at least one x-ray detector for collecting x-ray fluorescence from the focal point on the sample and directing the fluorescent x-rays of a characteristic energy of a predetermined analyte towards the at least one x-ray detector; and providing at least one excitation optic disposed between the at least one x-ray radiation source and a sample to be analyzed for collecting x-ray radiation from the at least one source and focusing the x-ray radiation to the focal point on the sample to incite said analyte in the sample to fluoresce.

35. The XRF spectroscopy method of claim 34, wherein the at least one source of x-ray radiation comprises at least one electron bombardment x-ray source.

36. The XRF spectroscopy method of claim 34, wherein the at least one excitation optic comprises at least one focusing polychromatic optic.

37. The XRF spectroscopy method of claim 36, wherein the at least one focusing polychromatic optic comprises at least one polycapillary optic.

38. The XRF spectroscopy method of claim 34, wherein the at least one excitation optic comprises at least one focusing monochromatic optic.

39. The XRF spectroscopy method of claim 38, wherein the at least one focusing monochromatic optic comprises at least one doubly curved crystal.

40. The XRF spectroscopy method of claim 38, wherein the at least one focusing monochromatic optic comprises at least one doubly curved multi-layer optic.

41. The XRF spectroscopy method of claim 34, wherein the focal point has a focal spot size less than 500 microns.

42. The XRF spectroscopy method of claim 34, wherein the sample comprises a solid.

43. The XRF spectroscopy method of claim 34, wherein the sample comprises a fluid.

44. The XRF spectroscopy method of claim 43, wherein the fluid comprises a petroleum based product.

45. The XRF spectroscopy method of claim 44, wherein the petroleum based product comprises gasoline or diesel.

46. The XRF spectroscopy method of claim 45, wherein the at least one analyte comprises sulfer.

47. The XRF spectroscopy method of claim 34, wherein the at least one doubly curved diffracting optic comprises at least one doubly curved crystal.

48. The XRF spectroscopy method of claim 47, wherein the at least one doubly curved crystal comprises at least one doubly curved crystal having Johann geometry.

49. The XRF spectroscopy method of claim 47, wherein the at least one doubly curved crystal comprises at least one doubly curved crystal having Johannson geometry or partial Johannson geometry approximation.

50. The XRF spectroscopy method of claim 47, wherein the at least one doubly curved crystal comprises at least one doubly curved logarithmic spiral crystal optic.

51. The XRF spectroscopy method of claim 34, wherein the at least one doubly curved diffracting optic comprises at least one doubly curved multi-layer optic.

52. The XRF spectroscopy method of claim 51, wherein the at least one doubly curved multi-layer optic comprises at least one doubly curved logarithmic spiral optic.

53. The XRF spectroscopy method of claim 34, wherein the at least one doubly curved diffracting optic comprises at least one doubly curved graded diffracting optic.

54. The XRF spectroscopy method of claim 34, wherein the at least one x-ray detector comprises at least one gas-proportional counter.

55. The XRF spectroscopy method of claim 34, wherein the at least one x-ray detector comprises at least one scintillation counter.

56. The XRF spectroscopy method of claim 34, wherein the at least one x-ray detector comprises a non-energy-sensitive detector.

57. The XRF spectroscopy method of claim 34, wherein the at least one doubly curved diffracting optic is positioned such that an input focal point thereof at the focal point of the sample corresponds to an output focal point of the at least one excitation optic.

* * * * *